(12) United States Patent
Ni et al.

(10) Patent No.: US 10,539,437 B2
(45) Date of Patent: Jan. 21, 2020

(54) CROP GROWTH SENSING APPARATUS AND METHOD SUPPORTING AGRICULTURAL MACHINERY VARIABLE-QUANTITY FERTILIZATION OPERATIONS

(71) Applicant: NANJING AGRICULTURAL UNIVERSITY, Nanjing (CN)

(72) Inventors: Jun Ni, Nanjing (CN); Weixing Cao, Nanjing (CN); Yan Zhu, Nanjing (CN); Shanshan Yu, Nanjing (CN); Yongchao Tian, Nanjing (CN); Xia Yao, Nanjing (CN); Fangrong Pang, Nanjing (CN); Lili Yao, Nanjing (CN); Fang Liu, Nanjing (CN)

(73) Assignee: NANJING AGRICULTURAL UNIVERSITY, Nanjing (CN)

( * ) Notice: Subject to any disclaimer, the term of this patent is extended or adjusted under 35 U.S.C. 154(b) by 14 days.

(21) Appl. No.: 16/066,802

(22) PCT Filed: Dec. 28, 2016

(86) PCT No.: PCT/CN2016/112803
§ 371 (c)(1),
(2) Date: Jun. 28, 2018

(87) PCT Pub. No.: WO2017/114438
PCT Pub. Date: Jul. 6, 2017

(65) Prior Publication Data
US 2019/0017853 A1    Jan. 17, 2019

(30) Foreign Application Priority Data

Dec. 28, 2015 (CN) ............................ 2015 1 1005093
Dec. 28, 2015 (CN) ............................ 2015 1 1008338

(51) Int. Cl.
*G01D 11/30* (2006.01)
*A01B 76/00* (2006.01)
(Continued)

(52) U.S. Cl.
CPC .............. *G01D 11/30* (2013.01); *A01B 76/00* (2013.01); *F16F 15/04* (2013.01); *G01D 11/10* (2013.01);
(Continued)

(58) Field of Classification Search
CPC ......... G01D 11/30; G01D 11/10; F16F 15/04; G01N 33/025
(Continued)

(56) References Cited

U.S. PATENT DOCUMENTS 6,540,039 B1    4/2003    Yu et al.
2004/0225703 A1    11/2004    Pangal
(Continued)

FOREIGN PATENT DOCUMENTS

CN    1070080 A    3/1993
CN    2500515 Y    7/2002
(Continued)

OTHER PUBLICATIONS

Li Shu-Qiang et. al, Research on Corn Growth Based on Vehicle-borne Ground-based Remote Sensing Dynamic Prediction, Journal of Henan Agricultural Sciences, 2014, 43(5), 196-200.
(Continued)

*Primary Examiner* — Jamel E Williams
(74) *Attorney, Agent, or Firm* — Gokalp Bayramoglu

(57) ABSTRACT

A crop growth sensing apparatus and method supporting agricultural machinery variable-quantity fertilization, includes a shock-absorbing support, a shock-absorbing frame, and a cantilever beam. The shock-absorbing support is connected to an agricultural machinery vehicle frame. The
(Continued)

cantilever beam is pivotally connected above a shock-absorbing spring of the shock-absorbing support. The cantilever beam, by means shock-absorbing springs mounted thereabove and thereunder, is pivotally connected to the shock-absorbing frame. The shock-absorbing frame is fixedly connected to a crop growth sensor. The crop growth sensing method employs an engine vibration model of the agricultural machinery and a vibration model for vehicle wheels and farmland road surface as excitations in analyzing vibrations of a crop growth multispectral sensor shock-absorbing apparatus to determine the number and mount positions of sensitive elements of the crop growth multispectral sensor. Also provided are a self-balancing apparatus and a self-balancing method for the crop growth multispectral sensor.

6 Claims, 7 Drawing Sheets

(51) Int. Cl.
*F16F 15/04* (2006.01)
*G01D 11/10* (2006.01)
*G01N 33/02* (2006.01)
*A01M 7/00* (2006.01)
*A01C 21/00* (2006.01)

(52) U.S. Cl.
CPC .......... *G01N 33/025* (2013.01); *A01C 21/007* (2013.01); *A01M 7/005* (2013.01); *F16F 2230/0011* (2013.01)

(58) Field of Classification Search
USPC .......................................................... 73/430
See application file for complete search history.

(56) References Cited

U.S. PATENT DOCUMENTS

| | | | |
|---|---|---|---|
| 2004/0232632 | A1 | 11/2004 | Beck et al. |
| 2016/0078570 | A1* | 3/2016 | Ethington .......... G06Q 10/1097 705/7.21 |
| 2016/0223511 | A1* | 8/2016 | Koshnick ................. G01N 1/08 |
| 2017/0261064 | A1* | 9/2017 | Liu .......................... B60R 11/04 |
| 2019/0178330 | A1* | 6/2019 | Schmid ................... F16F 1/121 |

FOREIGN PATENT DOCUMENTS

| | | | |
|---|---|---|---|
| CN | 101799844 | A | 8/2010 |
| CN | 101980249 | A | 2/2011 |
| CN | 102132645 | A | 7/2011 |
| CN | 102384767 | A | 3/2012 |
| CN | 202301728 | U | 7/2012 |
| CN | 202331207 | U | 7/2012 |
| CN | 103293156 | A | 9/2013 |
| CN | 103754080 | A | 4/2014 |
| CN | 104457936 | A | 3/2015 |
| CN | 104931218 | A | 9/2015 |
| CN | 105179887 | A | 12/2015 |
| CN | 105527970 | A | 4/2016 |
| CN | 105606145 | A | 5/2016 |
| DE | 19640277 | A1 | 3/1997 |
| JP | 2011247848 | A | 12/2011 |

OTHER PUBLICATIONS

Zhao Ying, Finite element analysis and structural optimization of chassis frame of planter for vehicle-borne port seedling machine, Chinese Master's Theses Full-text Database, Edition of Agriculture Science and Technology, Apr. 1, 2012. No. 8, 1-78.

* cited by examiner

CROP GROWTH SENSING APPARATUS AND METHOD SUPPORTING AGRICULTURAL MACHINERY VARIABLE-QUANTITY FERTILIZATION OPERATIONS

CROSS REFERENCE TO RELATED APPLICATIONS

This application is the national phase entry of International Application No. PCT/CN2016/112803, filed on Dec. 28, 2016, which is based upon and claims priority to Chinese Patent Application No. 201511008338.2, filed on Dec. 28, 2015 and Chinese Patent Application No. 201511005093.8, filed on Dec. 28, 2015 the entire contents of which are incorporated herein by reference.

TECHNICAL FIELD

The present invention relates to the field of precision agriculture, and specifically, to a crop growth sensing apparatus and method supporting agricultural machinery variable-quantity fertilization operations.

BACKGROUND

The variable-quantity fertilization technology is a core of the precision agriculture system. An intelligent variable-quantity fertilization operating system rapidly obtains information such as soil and crop growth statuses, and uses a crop nitrogen diagnosis model as a decision to change application of fertilizer in real time, so as to improve fertilizer utilization efficiency, reduce waste, protect the environment, and increase incomes of farmers. Obtaining crop growth information online is a primary condition for performing variable-quantity fertilization operations. Currently, crop growth spectrum monitoring mechanisms in China and abroad are all remote sensing methods of vertical angulation by using a sensitive element of a crop growth multispectral sensor. To be specific, the sensor is vertical to a crop canopy and performs static testing at a specific height. In agricultural machinery variable-quantity fertilization operations, because farmland roads are uneven, when traveling in the fields, agricultural machinery may tilt or bump. Consequently, the sensitive element of the crop growth multispectral sensor cannot perform vertical testing, directly affecting precision of crop canopy reflectance spectrum measurement. In addition, because of mechanical vibrations of the agricultural machinery, and because a sensitive element cantilever of the crop growth multispectral sensor is a weakly damped elastic body, when the agricultural machinery vibrates, the sensor vibrates correspondingly, resulting in that the sensor cannot obtain canopy reflectance spectrum information statically. Consequently, the measurement is accurate.

SUMMARY

With regard to the foregoing problems, the present invention provides a crop growth sensing apparatus and method supporting agricultural machinery variable-quantity fertilization operations, to reduce impacts of bumps, tilts, and vibrations generated in an agricultural machinery variable-quantity fertilization operation process on measurement performed by a crop growth multispectral sensor, thereby improving real-time information capturing precision of the sensor.

To achieve the foregoing objectives, the following technical solutions are used in the present invention:

A crop growth sensing apparatus supporting agricultural machinery variable-quantity fertilization operations includes a shock-absorbing support 2, a first shock-absorbing spring 3, a cantilever beam 5, a shock-absorbing frame 6, a second shock-absorbing spring 7, upper and lower plates 8, and a position-adjustable connecting plate 9, where the second shock-absorbing spring 7 and the first shock-absorbing spring 3 are respectively disposed above or under the cantilever beam 5, the cantilever beam 5 is pivotally connected to the shock-absorbing frame 6, the shock-absorbing frame 6 is fixedly connected to a crop growth sensor, one end of the shock-absorbing support 2 is fixedly connected to an agricultural machinery frame 1, the cantilever beam 5 is pivotally connected above the shock-absorbing spring 3 through a king pin 4, the shock-absorbing frame 6 is pivotally connected to the cantilever beam 5 by presetting a preload of the shock-absorbing spring 7 through the upper and lower plates 8, and the position-adjustable connecting plate 9 is configured to fixedly mount the crop growth sensor and adjust a height of the crop growth sensor.

Further, the crop growth sensor includes a crop growth multispectral sensor and a crop growth multispectral sensor self-balancing apparatus.

Further, the crop growth multispectral sensor self-balancing apparatus includes a simple pendulum gear damping system, a simple pendulum non-circular gear damping system, a simple pendulum gear driving system, and a control assembly; the crop growth multispectral sensor self-balancing apparatus may mount the apparatus on the agricultural machinery frame by means of a fastening plate 16; a first gear 10, a second gear 11, a third gear 13, and a fourth gear 14 form the simple pendulum gear damping system; a non-circular gear 19 and a non-circular gear 20 form the simple pendulum non-circular gear damping system, configured to inhibit an impact of a tilt of agricultural machinery; the simple pendulum gear damping system constituted by the first gear 10, the second gear 11, the third gear 13, and the fourth gear 14 is mounted on a frame 15; both of the third gear 13 and the fourth gear 14 are mounted on the fastening plate 16 by means of a shaft pin 25 with a bearing, and the non-circular gear 19 and the non-circular gear 20 are mounted on the frame 15 respectively by means of a first shaft pin 21 with a bearing and a second shaft pin 23 with a bearing; a crop growth multispectral sensor 12 is mounted on a position-adjustable plate 22; a gyroscope detects attitude information of the crop growth multispectral sensor 12, and applies, according to a predetermined target, a control signal to a simple pendulum gear pair and the simple pendulum gear driving system constituted by a first brushless motor driver 17, a second brushless motor driver 18, and a third brushless motor driver 24; a target control signal implements closed-loop control on the crop growth multispectral sensor in a balanced and steady state by using a PID control strategy based on an excitation-response model; and the control assembly includes a processor and a gyroscope, where the gyroscope detects attitude information of the crop growth multispectral sensor, and the processor controls, according to the attitude information of the crop growth multispectral sensor, a driver assembly of the brushless motor to control the simple pendulum gear (hiving system to drive the frame assembly to perform attitude adjustment on the crop growth multispectral sensor, to ensure that a angle between the crop growth multispectral sensor and a monitored crop is always kept within a range.

A simple pendulum gear pair system is used as a damping system and a driving system of the crop growth multispectral sensor self-balancing apparatus.

A crop growth sensing method supporting agricultural machinery variable-quantity fertilization operations includes the following steps:

(1) A method for determining the number of and positions of mounted crop growth sensors includes:

performing vibration finite element analysis on a crop growth sensor shock-absorbing frame by using ANSYS software;

during analysis, applying vibration models of agricultural machinery, including an engine vibration model of the agricultural machinery and a vibration model for vehicle wheels and a farmland road surface, to a model as excitation inputs;

respectively analyzing vibration amounts of crop growth sensors mounted at different positions of a cantilever beam, to obtain vibration amplitudes of the different positions; and obtaining a union set of mount positions satisfying the following two conditions:

[1] in a vibration condition, a distance H between a crop growth multispectral sensor and a crop=a mounting height $H_s$ of the crop growth multispectral sensor±a vibration amplitude $H_v$ satisfies that a lowest monitoring height $H_L$ of the crop growth multispectral sensor≤H≤a highest monitoring height $H_H$ of the crop growth multispectral sensor; and

[2] a diameter R of the field of view of the crop growth multispectral sensor≤a mounting distance L of the crop growth multispectral sensor≤1.5R.

Further, vibration finite element analysis is performed on the crop growth sensor shock-absorbing frame by using the ANSYS software, and the number of and mount positions of the crop growth sensors are determined with reference to a size of the field of view of the crop growth multispectral sensor, to achieve an optimal crop growth monitoring effect.

(2) A crop growth multispectral sensor self-balancing method includes:

for kinetic analysis and dynamic analysis, finding a response model of a crop growth multispectral sensor self-balancing apparatus under different excitations by means of numerical simulation and experiment analysis methods, where a gear engagement force $F_n$ of a simple pendulum gear, a length L between an engagement point and a pivot point, and a sensor weight in are all related to the response model, and their relationship is:

$$\theta(t) = A\cos\left[\sqrt{\frac{g + \frac{F_n}{m} \pm \frac{df(t)}{dt}}{L}} t + \varphi\right]$$

where A and φ are constants, depending on an initial state of the simple pendulum gear, and f(t) is an applied excitation; and designing a PID control algorithm according to an excitation-response model of the crop growth multispectral sensor self-balancing apparatus, to implement closed-loop control on a crop growth multispectral sensor in a balanced and steady state.

The present invention has beneficial effects:

The crop growth sensing apparatus supporting agricultural machinery variable-quantity fertilization operations of the present invention can improve accuracy of monitored information of the crop growth multispectral sensor, prevent tilts and unit vibrations during an agricultural machinery operation process from causing a problem of a poor monitoring effect of the crop growth multispectral sensor, and improve precision of real-time information capturing of the sensor.

Moreover, a crop growth sensing method supporting agricultural machinery variable-quantity fertilization operations provided by the present invention is beneficial to finding a strategy of closed-loop control on the crop growth multispectral sensor in a balanced and steady state, the number of mounted crop growth sensors, and mount positions thereof. Therefore, the crop growth sensing apparatus and method supporting agricultural machinery variable-quantity fertilization operations provided by the present invention provide important help in inhibiting impacts of tilts and unit vibrations during agricultural machinery operation on the crop growth multispectral sensor and improving monitored information of the sensor.

DETAILED DESCRIPTION OF THE EMBODIMENTS

Figure 1:
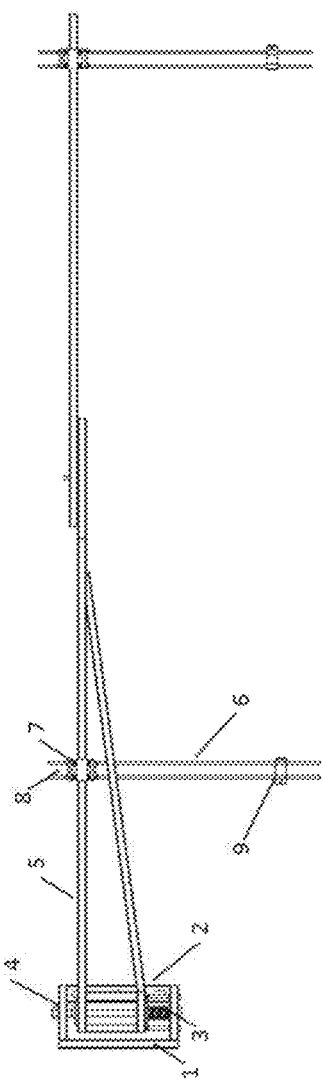
FIG. 1 is a schematic structural diagram of a crop growth multispectral sensor shock-absorbing apparatus according to the present invention.
Figure 2:
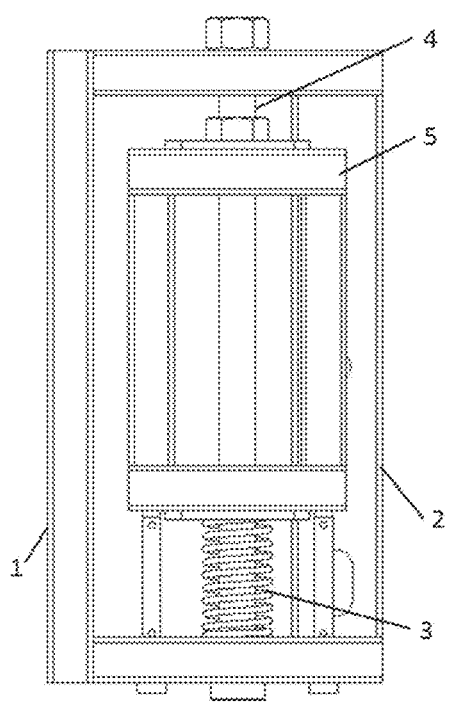
FIG. 2 is a schematic diagram of a shock-absorbing support and its mounting according to the present invention.
Figure 3:
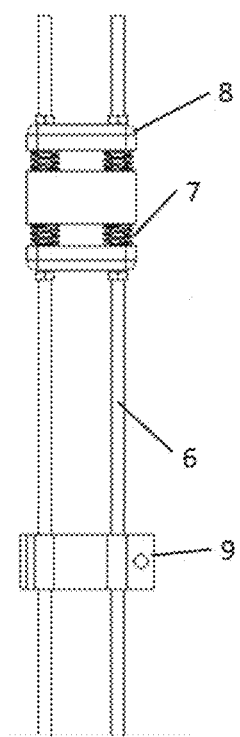
FIG. 3 is a schematic diagram of a shock-absorbing frame and its mounting according to the present invention.
Figure 4:
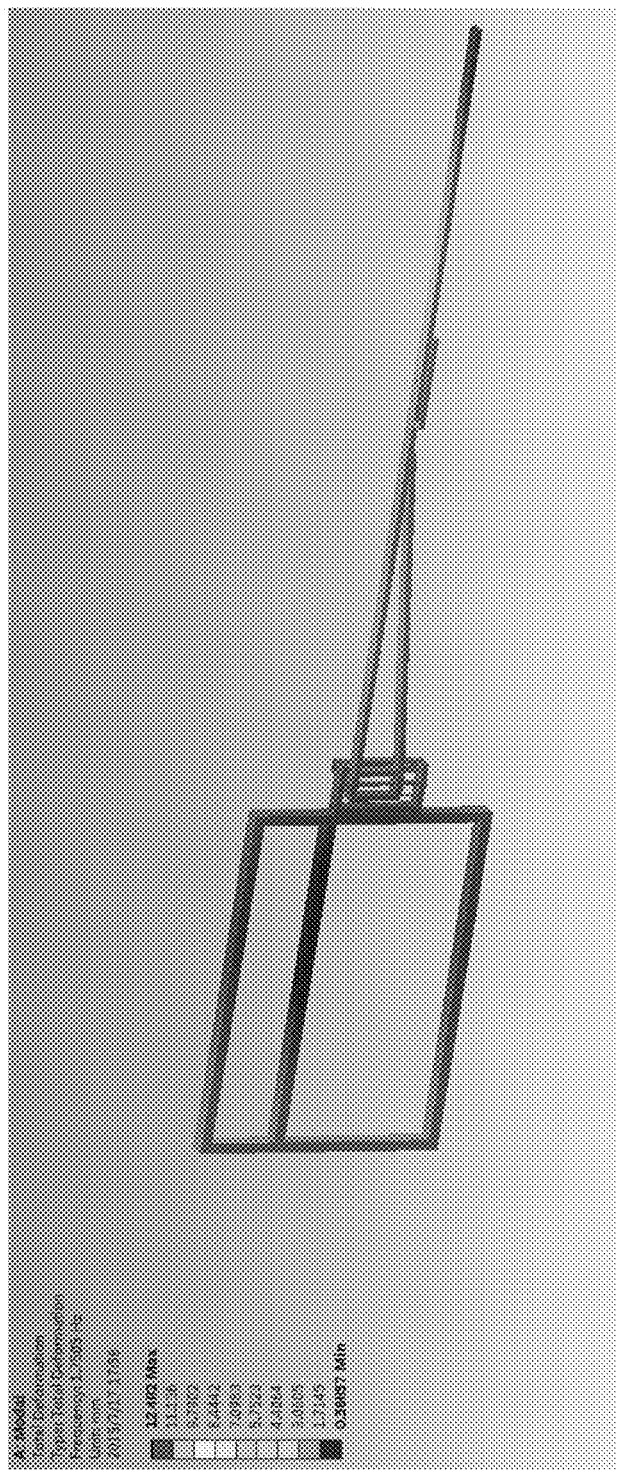
FIG. 4 is a schematic diagram of a result of ANSYS-based vibration modal analysis on a mounting frame according to the present invention.

The present invention is further described below with reference to the accompanying drawings.

A preferred embodiment of the present invention is shown in FIG. 1, FIG. 2, FIG. 3, and FIG. 4: In a crop growth sensing apparatus supporting agricultural machinery, variable-quantity fertilization operations, a crop growth multispectral sensor shock-absorbing apparatus thereof includes a shock-absorbing support 2, a first shock-absorbing spring 3, a cantilever beam 5, a shock-absorbing frame 6, a second shock-absorbing spring 7, upper and lower plates 8, and a position-adjustable connecting plate 9, where the second shock-absorbing spring 7 and the first shock-absorbing spring 3 are respectively disposed above or under the cantilever beam 5, the cantilever beam 5 is pivotally connected to the shock-absorbing frame 6, the shock-absorbing frame 6 is fixedly connected to a crop growth sensor, one end of the shock-absorbing support 2 is fixedly connected to an agricultural machinery frame 1, the cantilever beam 5 is pivotally connected above the shock-absorbing spring 3 through a king pin 4, the shock-absorbing frame 6 is pivotally connected to the cantilever beam 5 by presetting a preload of the shock-absorbing spring 7 through the upper and lower plates 8, and the position-adjustable connecting plate 9 is configured to fixedly mount the crop growth sensor and adjust a height of the crop growth sensor.

Figure 5:
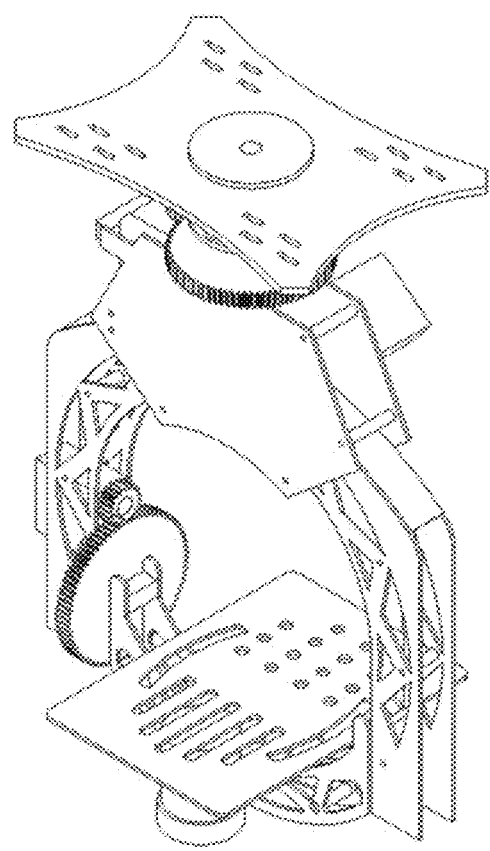
FIG. 5 is a schematic structural diagram 1 of a crop growth multispectral sensor self-balancing apparatus according to the present invention.
Figure 6:
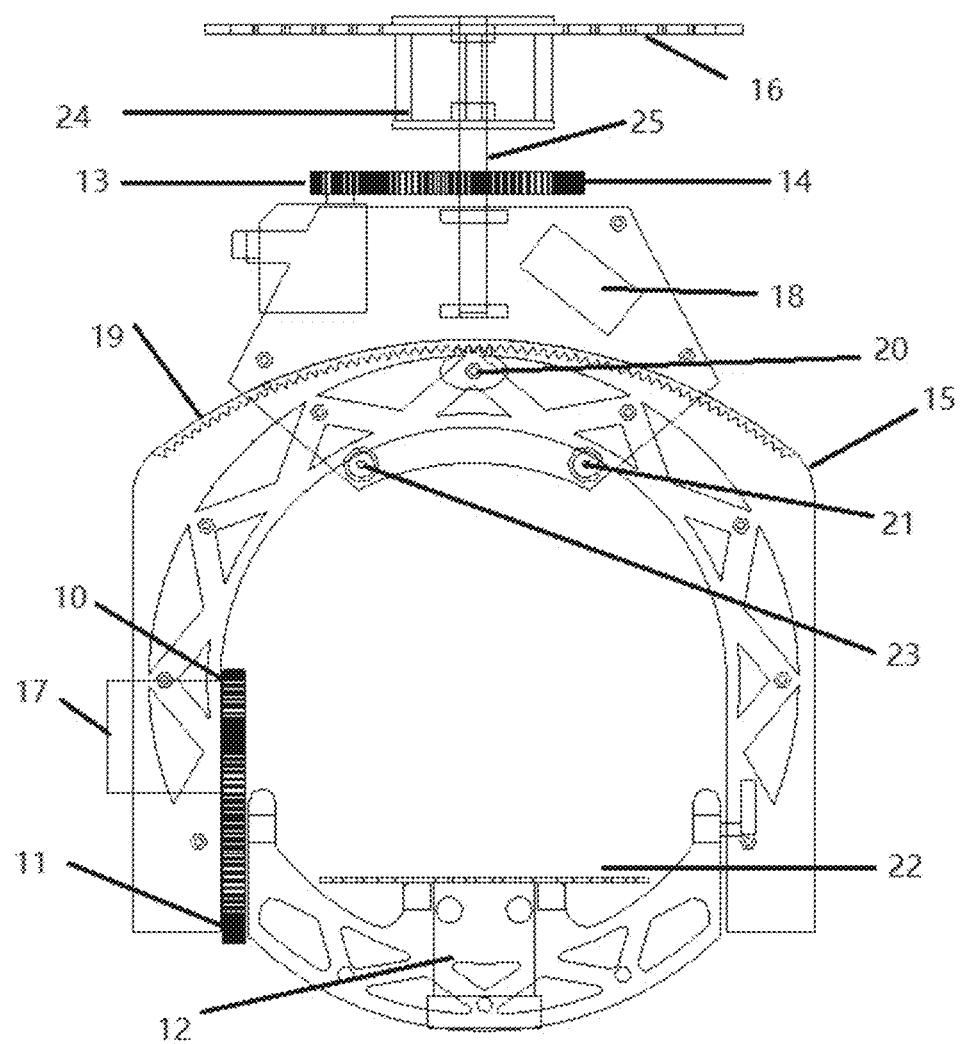
FIG. 6 is a schematic structural diagram 2 of a crop growth multispectral sensor self-balancing apparatus according to the present invention.
Figure 7:
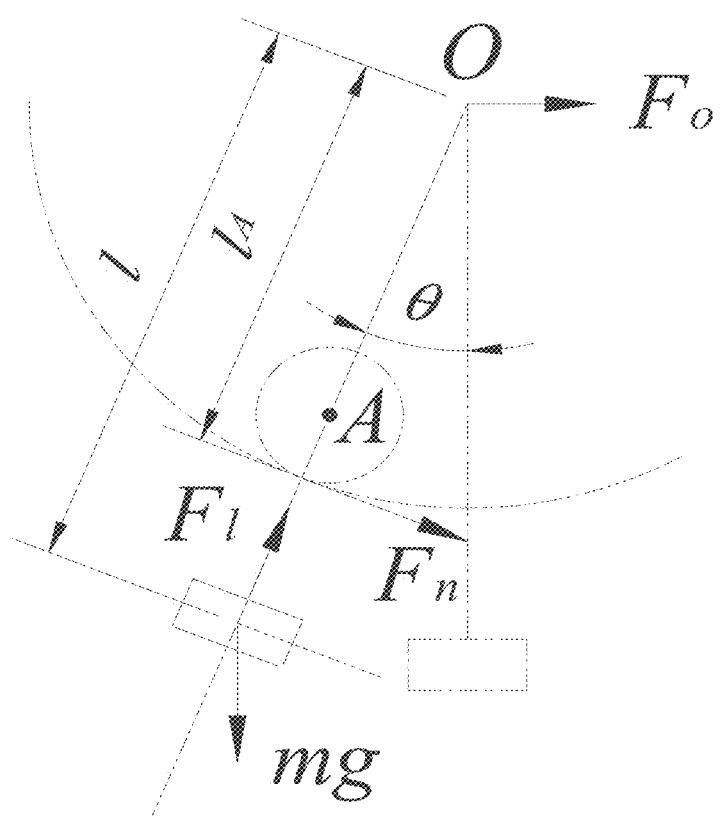
FIG. 7 is a principle diagram of a simple pendulum damping system according to the present invention.

A preferred embodiment of the present invention is shown in FIG. 5, FIG. 6, and FIG. 7: In a crop growth sensing apparatus supporting agricultural machinery variable-quantity fertilization operations, a crop growth multispectral sensor self-balancing apparatus thereof includes a simple pendulum gear damping system, a simple pendulum non-circular gear damping system, a simple pendulum gear driving system, and a control assembly; the crop growth multispectral sensor self-balancing apparatus may mount the apparatus on the agricultural machinery frame by means of a fastening plate 16; a first gear 10, a second gear 11, a third gear 13, and a fourth gear 14 form the simple pendulum gear damping system; a non-circular gear 19 and a non-circular gear 20 form the simple pendulum non-circular gear damping system, configured to inhibit an impact of a tilt of agricultural machinery; the simple pendulum gear damping system constituted by the first gear 10, the second gear 11, the third gear 13, and the fourth gear 14 is mounted on a frame 15; both of the third gear 13 and the fourth gear 14 are mounted on the fastening plate 16 by means of a shaft pin 25 with a bearing, and the non-circular gear 19 and the non-circular gear 20 are mounted on the frame 15 respectively by means of a first shaft pin 21 with a bearing and a second shaft pin 23 with a bearing; a crop growth multispectral sensor 12 is mounted on a position-adjustable plate 22; a gyroscope detects attitude information of the crop growth multispectral sensor 12, and applies, according to a predetermined target, a control signal to a simple pendulum gear pair and the simple pendulum gear driving system constituted by a first brushless motor driver 17, a second brushless motor driver 18, and a third brushless motor driver 24; a target control signal implements closed-loop control on the crop growth multispectral sensor in a balanced and steady state by using a PID control strategy based on an excitation-response model; and the control assembly includes a processor and a gyroscope, where the gyroscope detects attitude information of the crop growth multispectral sensor, and the processor controls, according to the attitude information of the crop growth multispectral sensor, a driver assembly of the brushless motor to control the simple pendulum gear driving system to drive the frame assembly to perform attitude adjustment on the crop growth multispectral sensor, to ensure that a angle between the crop growth multispectral sensor and a monitored crop is always kept within a range.

A simple pendulum gear pair system is used as a damping system and a driving system of the crop growth multispectral sensor self-balancing apparatus.

A crop growth sensing method supporting agricultural machinery variable-quantity fertilization operations includes the following steps:

(1) A method for determining the number of and positions of mounted crop growth sensors includes:

performing vibration finite element analysis on a crop growth sensor shock-absorbing frame by using ANSYS software;

during analysis, applying vibration models of agricultural machinery, including an engine vibration model of the agricultural machinery and a vibration model for vehicle wheels and a farmland road surface, to a model as excitation inputs;

respectively analyzing vibration amounts of crop growth sensors mounted at different positions of a cantilever beam, to obtain vibration amplitudes of the different positions; and obtaining a union set of mount positions satisfying the following two conditions:

[3] in a vibration condition, a distance H between a crop growth multispectral sensor and a crop=a mounting height $H_s$ of the crop growth multispectral sensor±a vibration amplitude $H_v$ satisfies that a lowest monitoring height $H_L$ of the crop growth multispectral sensor≤H≤a highest monitoring height $H_H$ of the crop growth multispectral sensor; and

[4] a diameter R of the field of view of the crop growth multispectral sensor≤a mounting distance L of the crop growth multispectral sensor≤1.5R. Further, vibration finite element analysis is performed on the crop growth sensor shock-absorbing frame by using the ANSYS software, and the number and mount positions of the crop growth sensors are determined with reference to a size of the field of view of the crop growth multispectral sensor, to achieve an optimal crop growth monitoring effect.

(2) A crop growth multispectral sensor sell-balancing method includes:

as shown in FIG. 7, for kinetic analysis and dynamic analysis, finding a response model of a crop growth multispectral sensor self-balancing apparatus under different excitations by means of numerical simulation and experiment analysis methods, where a gear engagement force $F_n$ of a simple pendulum gear, a length L between an engagement point and a pivot point, and a sensor weight m are all related to the response model, and their relationship is:

$$\theta(t) = A\cos\left[\sqrt{\frac{g + \frac{F_n}{m} \pm \frac{df(t)}{dt}}{L}} t + \varphi\right]$$

where A and φ are constants, depending on an initial state of the simple pendulum gear, and f(t) is an applied excitation; and designing a PID control algorithm according to an excitation-response model of the crop growth multispectral sensor self-balancing apparatus, to implement closed-loop control on a crop growth multispectral sensor in a balanced and steady state.

The foregoing embodiments are merely descriptions on preferred implementations of the present invention, rather than limitations to the concept and scope of the present invention. Various variations and improvements made by a person of ordinary skill in the art on the technical solutions of the present invention without departing from the design concept of the present invention shall all fall within the protection scope of the present invention. The technical contents claimed by the present invention are all recorded in the claims.

What is claimed is:

1. A crop growth sensing apparatus supporting agricultural machinery variable-quantity fertilization operations, comprising a shock-absorbing support, a first shock-absorbing spring, a cantilever beam, a shock-absorbing frame, a second shock-absorbing spring, upper and lower plates, and a position-adjustable connecting plate, wherein the first shock-absorbing spring is disposed between the cantilever beam and the shock-absorbing support to implement vibration isolation between the cantilever beam and an agricultural machinery frame; the second shock-absorbing spring is disposed between the shock-absorbing frame and the cantilever beam to implement vibration isolation between the sensor and the cantilever beam; the cantilever beam is pivotally connected to the shock-absorbing frame; the shock-absorbing frame is fixedly connected to a crop growth sensor; one end of the shock-absorbing support is fixedly connected to the agricultural machinery frame; the cantilever beam is pivotally connected above the shock-absorbing spring through a king pin; the shock-absorbing frame is pivotally connected to the cantilever beam by presetting a preload of the second shock-absorbing spring through the upper and lower plates; and the position-adjustable connecting plate is configured to fixedly mount the crop growth sensor and adjust a height of the crop growth sensor.

2. A crop growth multispectral sensor self-balancing apparatus, comprising a simple pendulum gear damping system, a simple pendulum non-circular gear damping system, a simple pendulum gear driving system, and a control assembly, wherein the crop growth sensor self-balancing apparatus is mounted on an agricultural machinery frame by means of a fastening plate; a first gear; a second gear, a third gear, and a fourth gear form the simple pendulum gear damping system; a first non-circular gear and a second non-circular gear form the simple pendulum non-circular gear damping system, wherein the simple pendulum gear damping system and the simple pendulum non-circular gear damping system are configured to inhibit an impact of a tilt of an agricultural machinery; the simple pendulum gear damping system constituted by the first gear, the second gear, the third gear, and the fourth gear is mounted on a frame; the third gear and the fourth gear are mounted on the fastening plate by means of a third shaft pin with a third bearing, and the first non-circular gear and the second non-circular gear are mounted on the frame respectively by means of a first shaft pin with a first bearing and a second shaft pin with a second bearing; a crop growth multispectral sensor is mounted on a position-adjustable plate; a gyroscope detects attitude information of the crop growth multispectral sensor, and applies, according to a predetermined target, a target control signal to a simple pendulum gear pair and the simple pendulum gear driving system constituted by a first brushless motor driver, a second brushless motor driver, and a third brushless motor driver; the target control signal implements a closed-loop control on the crop growth multispectral sensor in a balanced and steady state by using a PID control strategy based on an excitation-response model; and the control assembly comprises a processor and the gyroscope; wherein the gyroscope detects attitude information of the crop growth sensor, and the processor controls, according to the attitude information of the crop growth multispectral sensor; an assembly of the first brushless motor driver; the second brushless motor driver and the third brushless motor driver to controls the simple pendulum gear driving system to drive the agricultural machinery frame to perform an attitude adjustment on the crop growth multispectral sensor, to ensure that a angle between the crop growth multispectral sensor and a monitored crop is always kept within a range.

3. The crop growth sensing apparatus according to claim 2, wherein a simple pendulum gear pair system is used as a damping system and a driving system of the crop growth multispectral sensor self-balancing apparatus.

4. A crop growth sensing method supporting agricultural machinery variable-quantity fertilization operations, comprising the following steps:
performing a vibration finite element analysis on a crop growth sensor shock-absorbing frame by using ANSYS software;
during analysis, applying vibration models of an agricultural machinery, comprising an engine vibration model of the agricultural machinery and a vibration model for vehicle wheels and a farmland road surface, to a model as excitation inputs;
respectively analyzing vibration amounts of crop growth sensors mounted at different positions of a cantilever beam, to obtain vibration amplitudes of the different positions;
obtaining a union set of mounting positions satisfying the following two conditions:
[1] $H=H_s \pm H_v$ and $H_L \leq H \leq H_H$, wherein in a vibration condition, H is a distance between a crop growth multispectral sensor and a crop; $H_s$ is a mounting height of the crop growth multispectral sensor; $H_v$ is a vibration amplitude; $H_L$ is a lowest monitoring height of the crop growth multispectral sensor; and $H_H$ is a highest monitoring height of the crop growth multispectral sensor; and
[2] $R \leq L \leq 1.5R$, wherein R is a diameter of the field of view of the crop growth multispectral sensor; and L is a mounting distance of the crop growth multispectral sensor.

5. A crop growth multispectral sensor self-balancing method, comprising the following steps:
performing kinetic analysis and dynamic analysis; finding response models of a crop growth multispectral sensor self-balancing apparatus according to claim 2 under different excitations by means of numerical simulation and experiment analysis methods, wherein a gear engagement force of a simple pendulum gear, a length between an engagement point and a pivot point, and a sensor weight are all related to the response model, and their relationship is:

$$\theta(t) = A\cos\left[\sqrt{\frac{g + \frac{F_n}{m} \pm \frac{df(t)}{dt}}{L}} t + \varphi\right]$$

wherein A and $\varphi$ are constants, depending on an initial state of the simple pendulum gear, g is gravitational acceleration, $F_n$ is a gear engagement force of a simple pendulum gear, L is a length between an engagement point and a pivot point, m is a sensor weight, t is a simple pendulum swinging time and $f(t)$ is an applied excitation; and
designing a PID control algorithm according to an excitation-response model of the crop growth multispectral sensor self-balancing apparatus, to implement closed-loop control on a crop growth multispectral sensor in a balanced and steady state.

6. A crop growth multi spectral sensor self-balancing method, comprising the following steps:
performing kinetic analysis and dynamic analysis; finding response models of a crop growth multispectral sensor self-balancing apparatus according to claim 3 under different excitations by means of numerical simulation and experiment analysis methods, wherein a gear engagement force of a simple pendulum gear, a length between an engagement point and a pivot point, and a sensor weight are all related to the response model, and their relationship is:

$$\theta(t) = A\cos\left[\sqrt{\frac{g + \frac{F_n}{m} \pm \frac{df(t)}{dt}}{L}} t + \varphi\right]$$

wherein A and φ are constants, depending on an initial state of the simple pendulum gear, g is gravitational acceleration, $F_n$ is a gear engagement force of a simple pendulum gear, L is a length between an engagement point and a pivot point, m is a sensor weight, t is a simple pendulum swinging time and f(t) is an applied excitation; and designing a PID control algorithm according to an excitation-response model of the crop growth multispectral sensor self-balancing apparatus, to implement closed-loop control on a crop growth multispectral sensor in a balanced and steady state.

* * * * *